United States Patent [19]

Baasner et al.

[11] Patent Number: 4,622,427
[45] Date of Patent: Nov. 11, 1986

[54] PROCESS FOR THE PREPARATION OF PARTIALLY HYDROGENATED DERIVATIVES OF 2-NITRO-1,1,1-TRIFLUOROALKANES

[75] Inventors: Bernd Baasner, Leverkusen; Heinz Ziemann, Leichlingen; Erich Klaüke, Odenthal, all of Fed. Rep. of Germany

[73] Assignee: Bayer Aktiengesellschaft, Leverkusen, Fed. Rep. of Germany

[21] Appl. No.: 653,386

[22] Filed: Sep. 21, 1984

[30] Foreign Application Priority Data

Oct. 7, 1983 [DE] Fed. Rep. of Germany ....... 3336498

[51] Int. Cl.$^4$ ............................................ C07C 131/00
[52] U.S. Cl. .................................................. 564/261
[58] Field of Search ........................ 564/261, 300, 301

[56] References Cited

U.S. PATENT DOCUMENTS

| | | | |
|---|---|---|---|
| 2,233,823 | 3/1941 | Susie et al. | 564/261 |
| 2,423,180 | 7/1947 | Doumani et al. | 564/261 |
| 2,967,200 | 1/1961 | Foster et al. | 564/300 |
| 3,104,261 | 9/1963 | Young | 564/261 |
| 3,256,209 | 6/1966 | Young | 564/261 |
| 3,267,142 | 8/1966 | Young | 564/261 |
| 3,393,237 | 7/1968 | Forman et al. | 564/300 |
| 3,492,350 | 1/1970 | Young | 564/261 |

FOREIGN PATENT DOCUMENTS

| | | | |
|---|---|---|---|
| 186237 | 7/1956 | Austria | 564/261 |
| 800529 | 8/1958 | United Kingdom . | |

OTHER PUBLICATIONS

Journal of Catalysis, 82, pp. 56–65 (1983), Hydrogenation of Nitrocompounds with Supported Palladium Catalysts: Influence of Metal Dispersion and Nitrocompound Nature.

*Primary Examiner*—Natalie Trousof
*Assistant Examiner*—L. Hendriksen
*Attorney, Agent, or Firm*—Sprung, Horn, Kramer & Woods

[57] ABSTRACT

Partially hydrogenated derivatives of 2-nitro-1,1,1-trifluoroalkanes, in particular 2-oximino- and 2-hydroxylamino-1,1,1-trifluoroalkanes, are prepared by catalytically hydrogenating 2-nitro-1,1,1-trifluoroalkanes until a maximum of 2.2 moles of hydrogen per mole of 2-nitro-1,1,1-trifluoroalkane have reacted.

14 Claims, No Drawings

PROCESS FOR THE PREPARATION OF PARTIALLY HYDROGENATED DERIVATIVES OF 2-NITRO-1,1,1-TRIFLUOROALKANES

The present invention relates to a new process for the preparation of partially hydrogenated derivatives of 2-nitro-1,1,1-trifluoroalkanes, in particular a process for the preparation of 2-oximino- and 2-hydroxylamino-1,1,1-trifluoroalkanes.

The preparation of oximes containing fluorine by reacting the corresponding aldehydes or ketones with hydroxylamine has already been disclosed (see, for example, J. Org. Chem. 31, 964 (1966)) However, the aldehydes and ketones necessary as starting materials in this reaction are accessible only by elaborate processes and in moderate yields (see Bull. Sci. Acad. Roy. Belg. 13, 175 (1927) and J. Am. Chem. Soc. 72, 3371 (1950)), so that this route is not suitable for industrial application.

Hydroxylamines can be obtained from the oximes by reduction with borane (see J. Med. Chem. 13, 238 (1970)). This process is likewise unsuitable for technical application since boranes undergo spontaneous ignition and can only be manipulated with very elaborate safety measures.

In the hydrogenation of nitroalkanes containing no fluorine, the corresponding oximes and hydroxylamines can be obtained in only moderate yields and with only inadequate selectivity, and only by observing elaborate reaction conditions. Mixtures are produced, and these contain not only the desired oximes and/or hydroxylamines but also unreacted nitroalkane and completely hydrogenated products (amines) (see Houben-Weyl, Methoden der organischen Chemie (Methods of Organic Chemistry), volume IV, 1c, Part I, pages 496–497, published by George Thieme, Stuttgart, 1980). The main products of the catalytic hydrogenation of oximes are the corresponding amines, and the hydroxylamines result in only small amounts (see Houben-Weyl, loc. cit. pages 250–252) Recently, it has even been ruled out that an oxime occurs as an intermediate in the hydrogenation of nitroethane (see J. of Catalysis 82, 56–65 (1983)). In addition, it has to be expected that elimination of hydrogen fluoride takes place on hydrogenation of nitroalkanes containing fluorine.

Thus, there is as yet no industrially ulilizable process for the preparation of partially hydrogenated derivatives of 2-nitro-1,1,1-trifluoroalkanes, in particular of 2-oximino- and 2-hydroxylamino-1,1,1-trifluoroalkanes, and, from the facts applying to the hydrogenation of nitroalkanes containing no fluorine, it cannot be expected that it might be possible to prepare partially hydrogenated derivatives of 2-nitro-1,1,1-trifluoroalkanes on the basis of partial catalytic hydrogenation.

A process for the preparation of partially hydrogenated derivatives of 2-nitro-1,1,1-trifluoroalkanes has now been found, which process is characterised in that 2-nitro-1,1,1-trifluoroalkanes are catalytically hydrogenated until a maximum of 2.2 moles of hydrogen per mole of 2-nitro-1,1,1-trifluoroalkane have reacted.

The process according to the invention is particularly suitable for the preparation of 2-oximino- and 2-hydroxylamino-1,1,1-trifluoroalkanes. To prepare 2-oximino-1,1,1-trifluoroalkanes, the catalytic hydrogenation is preferably carried out until 0.7 to 1.2, particularly preferably 0.8 to 1.1, and very particularly preferably 1 mole of hydrogen per mole of 2-nitro-1,1,1trifluoroalkane has reacted. To prepare 2-hydroxylamino-1,1,1-trifluoroalkanes, the catalytic hydrogenation is preferably carried out until 1.9 to 2.2, particularly preferably 1.95 to 2.2, and very particularly preferably 2, moles of hydrogen per mole of 2-nitro-1,1,1-trifluoroalkane have reacted.

It is possible, for example, to use in the process according to the invention 2-nitro-1,1,1-trifluoroalkanes of the formula (I)

in which
R represents hydrogen, an alkyl radical having 1 to 15 C atoms, or a cycloalkyl radical having 5 to 8 C atoms.

In formula (I), R preferably represents hydrogen or an alkyl radical having 1 to 8 C atoms.

The 2-nitro-1,1,1-trifluoroalkanes to be used in the process according to the invention can be prepared from the corresponding olefins, for example by conjugated nitrofluorination (see Dokl. Akad. Nauk. SSR 149, 2222–2225 (1963) (Engl.) and Izvest Akad. Nauk. SSR 1963, 1794–1797 (Engl.) and the improvements on these processes according to German Offenlegungsschriften Nos. 3,305,201 and 3,305,202).

The process according to the invention can be carried out in the presence or absence of solvents. In general, it is advantageous to carry it out in the presence of a solvent, since this allows improved control of the hydrogenation which takes place exothermically.

Examples of suitable solvents are inert organic solvents. Examples of those suitable are alcohols, such as methanol, ethanol, ethylene glycol and diethylene glycol, ethers, such as dioxane, tetrahydrofuran, ethylene glycol monomethyl ether, ethylene glycol monoethyl ether, ethylene glycol dimethyl ether, diethylene glycol monomethyl ether and diethylene glycol dimethyl ether, saturated hydrocarbons, such as cyclohexane, or esters, such as ethyl acetate.

The course of the reaction can be controlled very well by adding water to the organic solvents. The hydrogenation can also be carried out in water itself, but the selectivity obtainable in this is generally lower than in the organic solvent. Methanol is preferably used as the solvent, and up to 20% by weight of water may be added to this. In this case, it is generally possible without difficulty to remove the solvents from the products of hydrogenation by distillation.

The process according to the invention can be carried out in reaction apparatus which is suitable for hydrogenation under atmospheric pressure and/or hydrogenation under elevated pressure. Examples of suitable materials for the reaction apparatus are glass, enamel, steel or stainless steel.

The pressure of hydrogen under which the hydrogenation is carried out can vary within wide limits. In general, the selectivity of the reaction increases with decrease in pressure. A pressure of 1 to 20 bar is preferred, and one of 1.2 to 8 bar is particularly preferred.

The reaction temperature can likewise be varied within wide limits, and can be, for example, between 0° and 120° C. Temperatures between 10° and 80° C. are particularly preferred, and those between 20° and 60° C. are very particularly preferred.

The hydrogenation takes place stepwise. In each instance, if the hydrogenation is stopped when the calculated amount of hydrogen has reacted, that is to say 1 mole of hydrogen per mole of 2-nitro-1,1,1-trifluoroalkane in the preparation of the oxime, and 2 moles of hydrogen per mole of 2-nitro-1,1,1-trifluoroalkane in the synthesis of the hydroxylamine, the particular product is obtained in optimum selectivity and yield. When 2-oximino-1,1,1-trifluoroalkanes are prepared in this manner, in each instance only small amounts of unchanged starting material and further hydrogenated products (hydroxylamines and amines) are detectable in the reaction product. When 2-hydroxylamino-1,1,1-trifluoroalkanes are prepared in this manner, only traces of the corresponding oxime are detectable in the reaction product in each instance. The formation of amines is generally observed only when the pressures of hydrogen are above 5 bar. However, the formation of amines is still relatively low in the pressure range 5 to 20 bar. Relatively large amounts of amines are only produced at pressures above 20 bar.

The reaction time necessary for the process according to the invention depends on the reaction rate, the partial pressure of hydrogen, the vigour of mixing the reaction mixture, and the activity and concentration of the hydrogenation catalyst. In general, the necessary reaction time ranges from 15 minutes to several hours.

The process according to the invention is carried out in the presence of hydrogenation catalysts. Examples of suitable hydrogenation catalysts are those which consist of or contain metals and/or compounds of elements of the eighth subgroup of the Mendeleev periodic table of the elements. The metals ruthenium, rhodium, palladium, platinum, cobalt and nickel, and their compounds, are preferred in the process. The metal compounds may, for example, be oxides, hydroxides and/or oxide hydrates. In addition, it is possible for the metals copper, vanadium, molybdenum, chromium and/or manganese, and compounds of these metals, to be present.

It is possible for the hydrogenation catalysts to consist entirely or predominantly of hydrogen-transfer substances, but these can also be applied to support materials. Examples of suitable support materials for the hydrogen-transfer substances are: inorganic materials, such as kieselguhr, silica, aluminas, alkali metal and alkaline earth metal silicates, aluminum silicates, montmorillonite, zeolites, spinells, dolomite, kaolin, magnesium silicates, zirconium oxide, zinc oxide, calcium carbonate, silicon carbide, aluminium phosphate, boron phosphate, asbestos, active charcoal or barium sulphate, but also organic materials, for example naturally occurring or synthetic compounds having high molecular weights, such as silk polyamides, polystyrenes, cellulose or polyurethanes. Inorganic support materials are preferred. The support material can be present in the form of, for example, beads, cords, threads, cylinders or polygons, or in the form of a powder.

Supported catalysts of these types can generally contain 0.5 to 50% by weight, preferably 1 to 10% by weight, of the hydrogen-transfer substance, relative to the total weight of the supported catalyst. The hydrogen-transfer substance can be homogeneously distributed in this support material, but catalysts in which the hydrogen-transfer substance is deposited in their outer layer or on their surface is preferred. The catalysts which can be used in the process according to the invention can be prepared and moulded in a known manner (see, for example, Houben-Weyl, Methoden der organischen Chemie, Volume IV, 1c, Part I, pages 16–26, published by Georg Thieme, Stuttgart 1980).

Preferred supported catalysts are ruthenium on charcoal, ruthenium on alumina, rhodium on charcoal, rhodium on alumina, palladium on charcoal, palladium on alumina, palladium on calcium carbonate, palladium on barium sulphate, palladium on silica, platinum on charcoal and platinum on alumina.

Examples of preferred hydrogenation catalysts which consist entirely or predominantly of hydrogen-transfer substance are oxide catalysts, such as palladium oxide, platinum oxide, ruthenium oxide and/or rhodium oxide/platinum oxide according to Nishimura, also black catalysts, such as palladium black, platinum black and rhodium black, which can be prepared by reduction of appropriate metal salts or mixtures of metal salts using alkali metal hydrides, alkali metal boranates, metal alkyls, hydrazine, formaldehyde, hydrogen or more electropositive metals.

Catalysts which are particularly preferred for the process according to the invention are palladium on charcoal, palladium on alumina, palladium on silica and palladium on calcium carbonate.

It is also possible to use, in particular for the preparation of 2-hydroxylamino-1,1,1-trifluoroalkanes, skeleton catalysts of the Raney type, Raney nickel being preferred.

In the process according to the invention, the hydrogenation catalyst can be used in amounts of, for example, 0.05 to 2.5% by weight of hydrogen-transfer substance, relative to the total weight of the reaction mixture. This amount is preferably 0.1 to 1% by weight.

It is also possible to use mixtures of two or more of the hydrogenation catalysts mentioned to carry out the process according to the invention.

In general, the catalytic activity of the hydrogenation catalysts is largely retained in carrying out the process according to the invention, so that, when the manner of operating is discontinuous, they can be repeatedly used and, when the manner of operating is continuous, they can remain in use for prolonged periods.

In a simple discontinuous embodiment, it is possible, for example, for the process according to the invention to be carried out as follows: an autoclave which is provided with a stirring or mixing device, and the temperature of which can be controlled, is charged with the 2-nitro-1,1,1-trifluoroalkane to be used, the hydrogenation catalyst and a solvent. Then hydrogen is injected until the desired pressure is reached, and the mixture is heated, with vigorous mixing, to the desired reaction temperature. The course of the reaction can easily be followed by measuring the consumption of hydrogen. Hydrogen consumed during the reaction can be replaced by continuous or discontinuous metering. Hydrogenation is stopped when the desired amount of hydrogen has been taken up. The hydrogenation can be stopped by cooling, ceasing mixing, releasing the pressure and/or removing the atmosphere of hydrogen. The reaction mixture can be worked up by, for example, first filtering off the catalyst, then distilling out the solvent and purifying the remaining reaction products by distillation or crystallisation. The process according to the invention can also be carried out continuously.

The partially hydrogenated derivatives of 2-nitro-1,1,1-trifluoroalkanes, in particular 2-oximino- and 2-hydroxylamino-1,1,1-trifluoroalkanes, which can be prepared according to the invention, have a known utility. H. K. Kim, H. K. Yaktin and R. E. Bambury describe in J. Med. Chem. 13, 238 (1970) the conversion of a 2-oximino-1,1,1-trifluoralkane to the corresponding hydroxylamine, several methods for the conversion of said hydroxylamine to α-(5-nitro-2-furyl)-N-cycloalkyl- and -N-alkyl-nitrones and their use as antibacterial, antifungal and anticoccidal agents.

Using the process according to the invention, it is possible to prepare partially hydrogenated derivatives of 2-nitro-1,1,1-trifluoroalkanes, in particular 2-oximino-1,1,1-trifluoroalkanes and 2-hydroxylamino-1,1,1-trifluoroalkanes, with high selectivity, and in good yields and high purities. Having regard to the facts applying to the hydrogenation of nitroalkanes containing no fluorine, which were mentioned in the introduction, it is to be regarded as extremely surprising that this is possible.

The examples which follow illustrate the present invention without restricting it in any way.

EXAMPLES

Example 1

Hydrogenation of 2-nitro-1,1,1-trifluoropropane to give 2-oximino-1,1,1-trifluoropropane 71.5 g (0.5 mol) of 2-nitro-1,1,1-trifluoropropane in 40 ml of methanol were hydrogenated, in a hydrogenation autoclave, in the presence of 5 g of palladium on calcium carbonate (5% palladium) under a pressure of 2 bar of hydrogen and at 25° to 30° C., until 0.5 mol of hydrogen had been taken up. The catalyst was then filtered off and washed with methanol. Examination of the filtrate by gas chromatography showed that it contained 2-nitro-1,1,1-trifluoropropane, 2-hydroxylamino-1,1,1-trifluoropropane and 2-oximino-1,1,1-trifluoropropane in the weight ratio 5:7:88.

The filtrate was fractionally distilled and this resulted in 49.4 g (78% of theory) of 2-oximino-1,1,1-trifluoropropane having a boiling point of 104 to 106° C.

Example 2

Hydrogenation of 2-nitro-1,1,1-trifluoropropane to give 2-hydroxylamino-1,1,1-trifluoropropane 71.5 g (0.5 mol) of 2-nitro-1,1,1-trifluoropropane in 40 ml of 95% aqueous methanol were hydrogenated, in a hydrogenation autoclave, in the presence of 0.5 g of palladium black under a pressure of 2 bar of hydrogen and at 45° to 50° C., until one mol of hydrogen had been taken up. The catalyst was then filtered off and washed with methanol, and the filtrate was evaporated to dryness under waterpump vacuum. 60.6 g (94% of theory) of 2-hydroxylamino-1,1,1-trifluoropropane remained, and its purity, found by gas chromatography, was 98.7%.

By recrystallizing a small sample of the resulting 2-hydroxylamino-1,1,1-trifluoropropane from n-hexane, colourless needles with a constant melting point of 88.5° to 89° C. were obtained.

Example 3

Hydrogenation of 2-nitro-1,1,1-trifluoroethane to give 2-oximino-1,1,1-trifluoroethane 64.5 g (0.5 mol) of 2-nitro-1,1,1-trifluoroethane in 50 ml of methanol were hydrogenated, in a hydrogenation autoclave, in the presence of 5 g of palladium on calcium carbonate (5% palladium) under a pressure of 1.9 bar of hydrogen and at 25° to 30° C., until 0.5 mol of hydrogen had been taken up. The catalyst was then filtered off and washed with methanol. Examination of the filtrate by gas chromatography showed that it contained 2-nitro-1,1,1-trifluoroethane, 2-hydroxylamino-1,1,1-trifluoroethane and 2-oximino-1,1,1-trifluoroethane in the weight ratio 10:14:76.

34.5 g (61% of theory) of 2-oximino-1,1,1-trifluoroethane were obtained with a boiling point of 89° to 94° C. by fractional distillation of the filtrate, and its purity on examination by gas chromatography was 96.3%.

Example 4

Hydrogenation of 2-nitro-1,1,1-trifluoroethane to give 2-hydroxylamino-1,1,1-trifluoroethane.

64.5 g (0.5 mol) of 2-nitro-1,1,1-trifluoroethane in 40 ml of 95% aqueous methanol were hydrogenated, in a hydrogenation autoclave, in the presence of 8 g of Raney nickel under a pressure of 2 bar of hydrogen, until one mol of hydrogen had been taken up. The catalyst was then filtered off and washed with methanol. The filtrate was dried over molecular sieves, and the methanol was distilled out over a 10 cm packed column. 53.5 g (93% of theory) of 2-hydroxylamino-1,1,1-trifluoroethane, of melting point 78° to 79° C., remained, and its purity on examination by gas chromatography was 96.5%.

What is claimed is:

1. A process for the preparation of 2-oximino- and 2-nitro-1,1,1-trifluoroalkanes consisting essentially of catalytically hydrogenating a 2-nitro-1,1-,1-trifluoroalkane of the formula

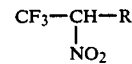

in which R is selected from the group consisting of hydrogen, an alkyl radical having 1 to 15 C atoms, and a cycloalkyl radical having 5 to 8 C atoms, with a catalyst containing a metal selected from the group consisting of ruthenium, rhodium, palladium, platinum, cobalt and nickel, until a maximum of 2.2 moles of hydrogen per mole of 2-nitro-1,1,1-trifluoroalkane have reacted.

2. A process according to claim 1, wherein R is hydrogen.

3. A process according to claim 1, wherein R is an alkyl radical having 1 to 8 carbon atoms.

4. A process according to claim 1, wherein R is methyl.

5. A process according to claim 1, wherein the process is carried out in the presence of a solvent.

6. A process according to claim 1, under a hydrogen pressure of 1 to 20 bar.

7. A process according to claim 1, wherein the process is carried out under the hydrogen pressure of 1.2 to 8 bar.

8. A process according to claim 1, wherein the process is carried out at 0° to 120° C.

9. A process according to claim 6, wherein the process is carried out at a temperature of 0° to 120° C.

10. A process according to claim 9, wherein the process is carried out at a temperature in the range of 10° to 80° C.

11. A process according to claim 1, for the preparation of 2-oximino-1,1,1-trifluoroalkane wherein the hydrogenation is carried out until 0.7 to 1.2 moles of hydrogen have reacted per mole of 2-nitro-1,1,1-trifluroalkane.

12. A process according to claim 1, wherein for the preparation of 2-hydroxyamino-1,1,1-trifluoroalkane, the hydrogenation is carried out until 1.9 to 2.2 moles of hydrogen per mole of 2-nitro-1,1,1-trifluoroalkane have reacted.

13. A process according to claim 10, wherein the process is carried out until 0.8 to 1.1 moles of hydrogen per mole of 2-nitro-1,1,1-trifluoroalkane have reacted.

14. A process according to claim 11, wherein the process is carried out until 1.95 to 2.2 moles of hydrogen per mole of 2-nitro-1,1,1-trifluoroalkane have reacted.

* * * * *

UNITED STATES PATENT AND TRADEMARK OFFICE
CERTIFICATE OF CORRECTION

PATENT NO. : 4,622,427

DATED : November 11, 1986

INVENTOR(S) : Bernd Baasner, et al.

It is certified that error appears in the above-identified patent and that said Letters Patent is hereby corrected as shown below:

Title Page, "No. [75] Inventors:", line 2  Delete "Erich Klauke" and substitute --Erich Klauke--

Signed and Sealed this

First Day of December, 1987

Attest:

DONALD J. QUIGG

Attesting Officer  Commissioner of Patents and Trademarks